United States Patent [19]

Blomqvist et al.

[11] Patent Number: 5,335,653
[45] Date of Patent: Aug. 9, 1994

[54] METHOD AND APPARATUS FOR DELIVERING A STABLE GAS MIXTURE TO A PATIENT

[75] Inventors: Kaj Blomqvist, Espoo; Mika Mustonen, Helsinki; Asko Saarelainen, Espoo; Pekka Meriläinen, Helsinki, all of Finland

[73] Assignee: Instrumentarium Corporation, Finland

[21] Appl. No.: 864,606

[22] Filed: Apr. 7, 1992

[30] Foreign Application Priority Data

Apr. 12, 1991 [FI] Finland ............... 911807

[51] Int. Cl.$^5$ ............................. A61M 16/00
[52] U.S. Cl. ..................... 128/204.18; 128/205.11; 128/718; 128/200.24
[58] Field of Search ............... 128/200.24, 203.12, 128/203.25, 204.18, 205.11, 204.29, 205.26, 718, 719

[56] References Cited

U.S. PATENT DOCUMENTS

| | | | |
|---|---|---|---|
| 3,680,557 | 8/1972 | Doniguian | 128/205.26 X |
| 3,786,809 | 1/1974 | Kitrilakis | 128/205.26 |
| 3,799,163 | 3/1974 | Heath | 128/205.26 |
| 4,407,280 | 10/1983 | Trammell | 128/205.26 |
| 4,620,538 | 11/1986 | Koegel | 128/201.23 |
| 4,763,664 | 8/1988 | Meriläinen | 128/718 |
| 4,832,042 | 5/1989 | Poppendiek | 128/730 |
| 5,040,541 | 8/1991 | Poppendiek | 128/718 |

FOREIGN PATENT DOCUMENTS

| | | | |
|---|---|---|---|
| 567038 | 5/1958 | Belgium | 128/205.26 |
| 2652136 | 3/1978 | Fed. Rep. of Germany | 128/200.24 |
| 3536519 | 11/1987 | Fed. Rep. of Germany | |
| 1261626 | 10/1986 | U.S.S.R. | 128/719 |
| 1219678 | 1/1971 | United Kingdom | 128/205.26 |
| 2220573 | 1/1990 | United Kingdom | 128/205.26 |

Primary Examiner—Edgar S. Burr
Assistant Examiner—Eric P. Raciti
Attorney, Agent, or Firm—Andrus, Sceales, Starke & Sawall

[57] ABSTRACT

A method and apparatus for delivering respiratory gases to a patient maintains a mixture of gases stable and minimizes the effects of ambient air leakage. Some of the gases supplied to a gas collection unit in which the patient's head is placed are by-passed to a buffer space that partially surrounds the gas collection unit. The volume of the buffer space stabilizes the mixture and outflow from the buffer space minimizes ambient air leakage into the gas collection unit. Gases from the gas collection unit are supplied to a measuring unit for analyzing the gas respired by the patient.

36 Claims, 4 Drawing Sheets

METHOD AND APPARATUS FOR DELIVERING A STABLE GAS MIXTURE TO A PATIENT

BACKGROUND OF THE INVENTION

The present invention relates to a method for mixing together gases flowing from two or more different gas sources and for maintaining the mixed gas concentration or composition as stable as possible and for passing such a gas to a gas collection unit, through which a patient's inhalation and exhalation occurs and from which gas collection unit flows gas to a measuring device for analysing the gas respired by a patient. The invention relates also to an apparatus comprised of a gas collection unit provided with a neck opening for placing the gas collection unit around the head of a patient and of a port for delivering to the gas collection unit the gas to be respired by a patient and of a port for passing the gas contained in the gas collection unit to a measuring device for effecting necessary measurements.

The human metabolism can be measured by means of so-called indirect calorimetry, wherein the concentrations and flow rates of respiratory gases can be measured to determine oxygen consumption (VO2) and carbon dioxide output (VCO2). The measuring results can be used to calculate an estimated energy consumption and respiratory quotient (RQ=VCO2/VO2) as well as the estimated amount of carbohydrates and fats consumed by the organism. The combustion of hydrocarbons produces as much carbon dioxide as it consumes oxygen, whereby RQ=1, while the combustion of fats produces a corresponding ratio of about 0.7.

Indirect calorimetry is particularly used in hospital intensive care units for determining the nutrition demand of critically ill patients who are fed intravenously or parenterally or by means of an abdominal tube or enterally. Since a large number of these patients are linked to a respiratory machine or a respirator, the mixing of inhalation gases and the collection of exhalation gases for a measuring operation directly from a patient's respiratory cycle is relatively simple. One device intended for measuring patients linked with a respirator is disclosed in the Finnish Patent No. 78231.

A demand for applying indirect calorimetry also to spontaneously respiring patients has been ever increasing. This concerns particularly patients having e.g. cancer and various metabolic diseases. One gas collection unit intended for metabolic measurements on spontaneously respiring patients has been disclosed in the Finnish Patent No. 78609. The gas collection unit is often referred to as a canopy.

During or after various medical procedures, the critically ill spontaneously respiring patients are fed with excess oxygen, if necessary. Also these types of adult and child patients, who suffer primarily from cardiac and pulmonary malfunction, are preferably subjected to metabolic measurements. The presently available gas collection units, like the one mentioned above, involve problems in metabolic measurements and those become evident at the time it is necessary to feed a patient with air containing more oxygen than ambient air. Thus, the gas collection unit should be completely sealed. When using a gas collection unit to respire air, the oxygen content of which is equal to that of ambient air, a slight leak is not crucial but, whenever the oxygen content in a gas collection unit differs from the ambient air, even a slight leak can result in a major measuring error and falsify e.g. the rates of energy consumption or respiratory quotient.

Furthermore, in a conventional gas collection unit, wherein a patient receives his or her inhalation air and in which a patient's exhalation air arrives, another source of problems is that, upon supplying excess oxygen into a gas flow running towards a gas collection unit, the patient's own respiration tends to alter the inlet flow and, thus, the oxygen content is constantly varying in synchronization with respiration. For purposes of measurements, the oxygen content should be constant.

SUMMARY OF THE INVENTION

An object of the present invention is to eliminate the above problems. The object is to provide a method and an apparatus for delivering a stable gas mixture to a patient. Another object is to provide a method and an apparatus for supplying a patient with a gas having a composition or concentration of ingredients contained therein which differs from ambient gas. A particular object is to provide a method and an apparatus, whereby a metabolic measurement to be performed on a patient can be carried out in a reliable manner. Hence, the object is to provide a method and an apparatus, whereby a gas having a higher oxygen content than the air surrounding a patient can be delivered to a patient while avoiding metabolic measuring errors. A still further object is to provide a method and an apparatus, whereby a gas having a higher oxygen content than the air surrounding a patient can be delivered to a patient while maintaining a constant oxygen content in the delivered gas. Yet another object is to provide a simple and economically priced apparatus for delivering to a patient a gas having a higher oxygen content than the air surrounding the patient.

The characterizing features of an apparatus according to the invention are set forth in the annexed claims.

According to the invention, a gas intended for a patient is mixed with another separately delivered gas prior to passing the gas flow into a gas collection unit, the patient inhaling a gas contained therein and the exhalation of a patient also proceeding through said gas collection unit. Usually, one of the gases is oxygen and the other is air. The gas collection unit usually extends around the head of a patient and terminates in a neck opening, sealed around the neck of a patient in order to prevent any gas leak out of the gas collection unit or vice versa. From the gas collection unit, preferably from a section in front of the mouth of a patient, a gas flow is passed to a measuring element for metabolic measurement.

In order to achieve a sufficient mixing of oxygen and air delivered from separate sources towards a gas collection unit prior to the arrival thereof in a gas collection unit to be respired by a patient, the inlet flow prior to a gas collection unit must exceed the measuring flow rate proceeding through the gas collection unit to a measuring device. This object is achieved by passing some of the flow coming towards a gas collection unit past said gas collection unit. The by-pass flow can be used to maintain stable air and oxygen contents and, thus, the oxygen can be uniformly mixed with the air current. Thus, the pressure fluctuations caused by a patient's inhalation and exhalation in a gas collection unit cannot affect the propagation of a flow approaching said gas collection unit, as otherwise this propagation would be alternately fast and alternately nearly stopped, resulting in fluctuations in the oxygen content of a gas arriving in a gas collection unit.

The gas flow by-passing the gas collection unit can either be deflected directly away, whereby the outgoing flow is no longer necessarily exploited in view of improving the operation of a gas collection unit, or preferably to serve as a cover or as a screen in front of one or a plurality of ports in a gas collection unit, whereby the object is to prevent the ambient air, whose oxygen content is different from that of the gas contained inside a gas collection unit, from penetrating inside a gas collection unit and causing instability in the oxygen content. The oxygen content of a gas by-passing the gas collection unit is of course equal to that of the gas delivered into the gas collection unit.

The gas collection unit is provided with at least one port through which the gas contained in the gas collection unit is in communication with ambient air. One of these ports or openings is used for placing a patient's head inside the gas collection unit. This opening is generally surrounded by resilient or flexible flaps or skirts which settle against the skin of a patient as the gas collection unit is fitted around the head of a patient. The flexible skirts are often made of plastics and their purpose is to prevent the passage of gas out from inside the gas collection unit and vice versa. However, they are not capable of totally sealing such flows. On the other hand, tightly sealed skirts that would be capable of preventing the flows often lead to structural designs which give a patient an insecure feeling and, thus, often result in sensations of apprehension. These sensations of apprehension or fear are reduced by constructing a gas collection unit which is readily removable even by patients themselves. Thus, a harmful flow, occurring through the skirts and hampering the measurements, cannot be totally eliminated. In the present invention, this problem is solved by covering the opening formed by said skirts with a gas by-passing said gas collection unit. A space in front of the opening, in this context referred to as a buffer space, is preferably at least partially insulated from its environment and, thus, the composition of a gas flow supplied therein also remains as stable as possible. The buffer space covering said opening is provided with its own gas outlet port which is also preferably located between a patient and the periphery of said buffer space.

The pressure prevailing inside a buffer space covering the opening of a gas collection unit should be higher than or preferably equal to the pressure prevailing inside a gas collection unit. This is to eliminate the undesired flow caused by a lower pressure prevailing outside the opening.

In a particularly preferred case, the air and the oxygen to be mixed therewith are delivered along a separate or especially a common line directly into a buffer space, wherein the gases mix with each other producing a stable gas mixture. Thus, some of the gas contained in a buffer space is passed into a gas collection unit to be respired by a patient and some of it elsewhere in the environment. At the same time, the gas in a buffer space prevents a detrimental flow occurring through one or several ports in a gas collection unit, which flow would have a detrimental effect on the stability of a gas presently inside said gas collection unit.

The buffer space has a volume which is preferably at least equal to the single respiratory volume of a patient and still more preferably higher than the highest possible single respiratory volume. In practice, the volume is approximately 3-5 liters.

BRIEF DESCRIPTION OF THE DRAWING

The invention will now be described in more detail with reference made to the accompanying drawings, in which.

DESCRIPTION OF THE PREFERRED EMBODIMENTS

Figure 1:
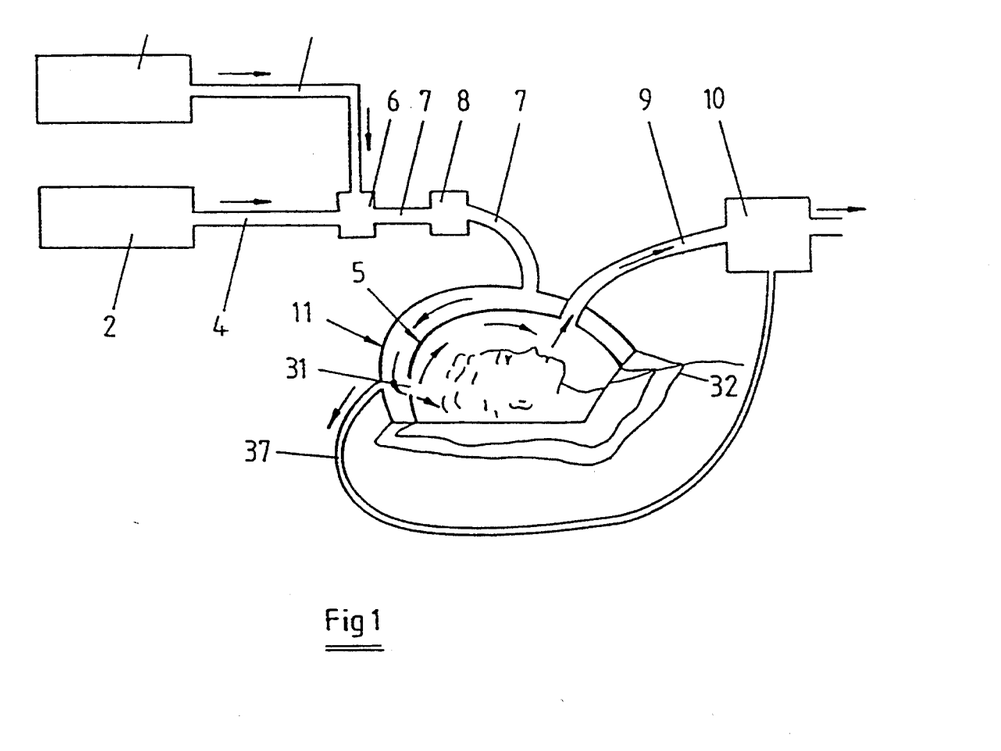
FIG. 1 is a schematic general view of one preferred arrangement of the invention for metabolic measurements on patients respiring a gas having a higher oxygen content than ambient air.

FIG. 1 illustrates one preferred embodiment for providing a patient's respiratory gas with an oxygen content higher than that of normal room air and for maintaining at the same time the oxygen content as stable as possible. In this figure, oxygen is contained in a gas source 1 while a gas source 2 carries a nitrogen-containing gas, preferably air. The oxygen running from gas source 1 travels along a line 3 to finally mix with air arriving from gas source 2 along a line 4. Mixing of the gases must be effected upstream of a gas collection unit 5 which is fitted around the head of a patient. In FIG. 1, said lines 3 and 4 join each other at an element 6. This element is used to adjust the relative ratio of oxygen and air to a desired level. From element 6 the combined gas flow travels along a line 7 to an element 8 controlling the overall flow rate and further towards gas collection unit 5. From the gas collection unit the flow continues along a line 9 to a measuring device 10 for metabolic measurements.

The measuring device is used to analyse the carbon dioxide content and oxygen content of a gas which is received from the gas collection unit and which contains a patient's exhalation gas. The aspiration of a measuring device produces a flow. Suitable measuring devices are commercially available, including e.g. a device described in the U.S. Pat. No. 4,856,531 for its essential components. This metabolic monitoring device is manufactured by Instrumentarium Oy Datex of Helsinki Finland and sold under the trademark DELTATRAC.

In view of the invention it is essential, however, that some of the gas flowing along lines 3 and 4 be deflected past a gas collection unit, whereby the flow through said gas collection unit is lesser than that running along lines 3 and 4. In the case of FIG. 1, the flow arriving along line 7 is deflected upstream of gas collection unit 5 into a separate buffer space 11.

Figure 2:
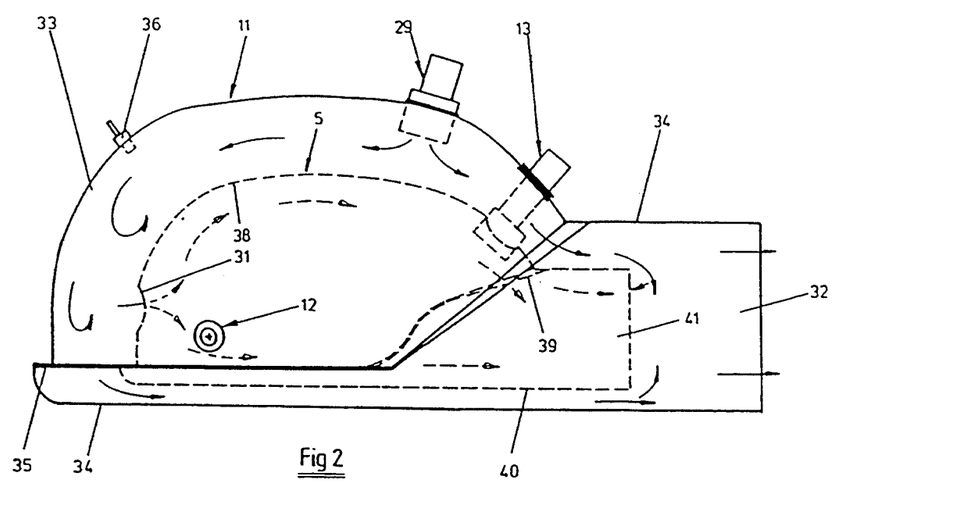
FIG. 2 shows in more detail an element fitted around the head of a patient and illustrated in FIG. 1.
Figure 3:
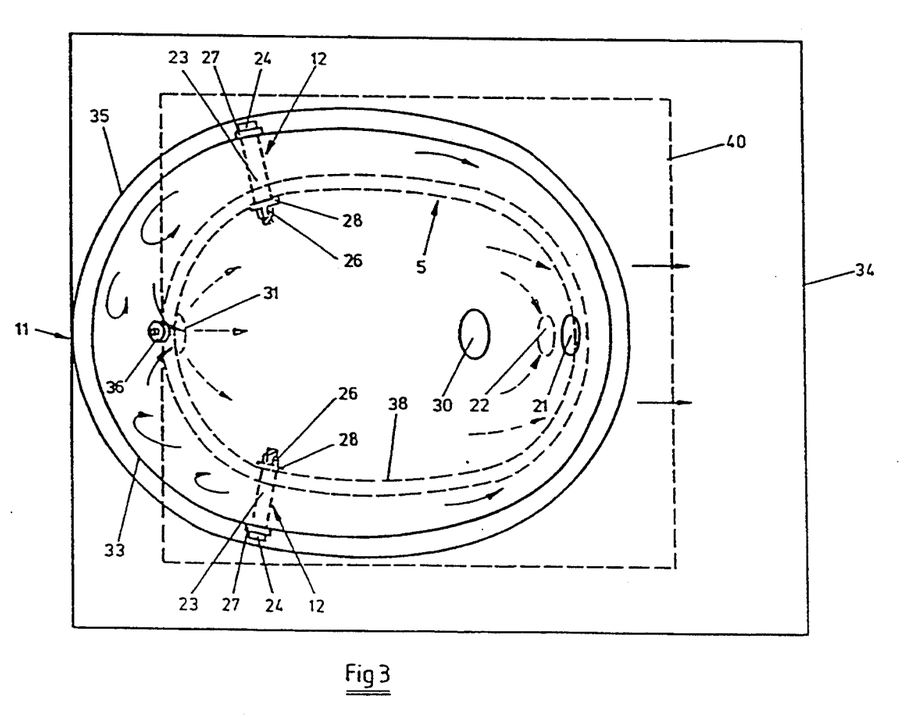
FIG. 3 is a general plan view of the element shown in FIG. 2.

FIGS. 2 and 3 show in more detail one preferred gas collection unit 5 and a buffer space 11, which in this embodiment encompasses the entire gas collection unit. The buffer space and gas collection unit are attached to each other by means of fastening elements 12 shows particularly in FIG. 3 and by means of a connecting pipe 13, joining the gas collector unit and the buffer space and shown in FIG. 2.

Figure 4:
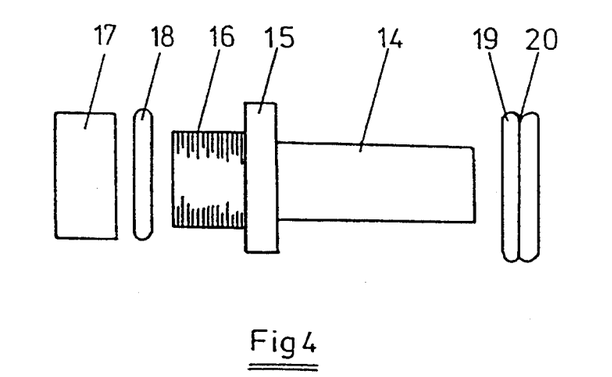
FIG. 4 is a more detailed view of a connecting pipe shown in FIG. 2.

The connecting pipe 13 is not shown in FIG. 3 but is illustrated in detail in FIG. 4 and it serves for its part to hold a gas collection unit and a buffer space together. In addition, the connecting pipe also serves as a passage for the gas discharging from the gas collection unit, i.e. it is used to deliver a gas exhaled by a patient from the gas collection unit through the buffer space along line 9 to measuring device 10 in a manner that the gas is not able to mix with a gas contained in the buffer space.

The connecting pipe 13 comprises a tubular base member 14 whose outer surface is surrounded by a thickening 15. On the other side of this thickening is a threading 16 for a screwable nut 17. Two annular seals 18 and 19 are also required. Along the outer edge of one 19 of these seals runs a groove 20 for securing the seal in a port 21 leading out of the buffer space. The other one 18 of these seals settles against thickening 15, whereafter the threaded end of said base member is inserted through an opening 22 between gas collection unit and buffer space and the nut is screwed on. This is followed by pushing the other end of a connecting pipe through said port 21 leading out of the buffer space as well as its surrounding seal 19.

Figure 5:
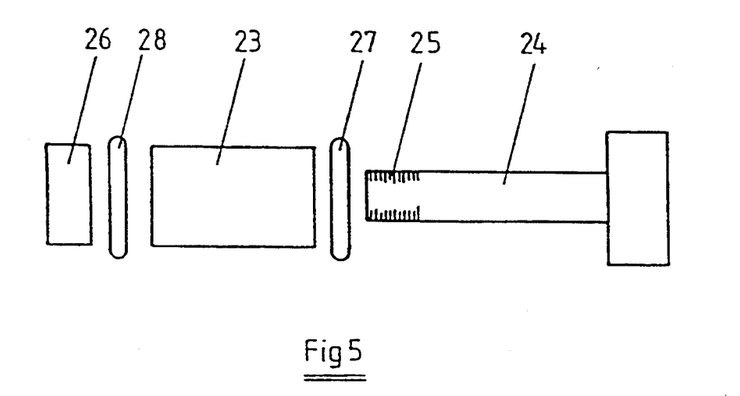
FIG. 5 is a more detailed view of a fastening element shown in FIG. 3.

This is followed by fitting the fastening elements 12 in position. The fastening element 12 is shown in more detail in FIG. 5 and comprises a hollow sleeve 23, fitted between gas collection unit and buffer space, and a bolt 24 insertable inside the sleeve and extending into spaces on either side of buffer space, as well as a nut 26 fitting said bolt threading 25. In addition, annular sealings 27 and 28 are fitted against the bolt head and the nut.

The gas from containers 1 and 2 flows along line 7 which is joined with a connecting member 29, which is in communication with buffer space 11 and through which the gas flows into the buffer space. The connecting member 29 is only shown in FIG. 2 and it is structurally very similar to connecting pipe 13. The most apparent difference is the absence of a grooved sealing 19, as connecting member 29 is only coupled to a port 30 leading to the buffer space.

The flow arriving in buffer space along line 7 finds its way particularly to those locations where the gas flow from inside the buffer space can continue its passage. One such location is an opening 31 between buffer space and gas collection unit, through which the flow coming out of buffer space finds its way into the gas collection unit. Another location is an inlet opening 32 shown in FIG. 2 at one end of the buffer space and through which the head of a patient is brought into the buffer space and into gas collection unit 5 fitted inside the buffer space.

The assembly surrounding said buffer space preferably comprises a hood 33 and a skirt 34. The hood is made of rather stiff transparent plastics for a patient to have a clear view around. The skirt is made of a flexible plastic sheet which is fastened to an extension 35 set around hood 33. As a patient lies on his or her back, it is good for comfort if flexible skirt 34 extends underneath the head. In the figures, the same skirt also surrounds inlet opening 32 which should be sealed against a patient protruding out of it, so that the ambient air surrounding buffer space 11 could not have too much effect on the gas composition or gas concentration prevailing inside the buffer space.

The buffer space hood 33 is also fitted with a coupling member 36 for aspirating a sample of a gas contained inside the buffer space along a line 37 shown in FIG. 1, said sample being aspirated at a slight flow rate to measuring device 10 for determining the oxygen content of a gas contained in the buffer space and inhaled by a patient. The same measuring device as described above is also capable of measuring the oxygen content. At this stage, as necessary measurements have been performed as described above on both a gas that arrived in measuring device from gas collection unit and contained a patient's exhalation gas and on a gas inhaled by a patient, it is possible to determine a respiratory quotient in a per se known manner.

A gas collection unit 5 shown in figures inside a buffer space is structurally highly similar to buffer space 11. Preferably, the gas collection unit also comprises a hood 38 and a skirt 40 fastened to its extension 39. Also in this case, the skirt extends underneath the head of a patient lying on his or her back and it extends up to a neck opening 41. As opposed to FIG. 2, said skirts 34 and 40 are shown in FIG. 3 in an extended condition. The flow directed outwards through the skirts of a gas collection unit should be prevented as strictly as possible. The critical point is neck opening 41, through which a gas collection unit is fitted around the head of a patient. The neck of an adult patient is usually positioned exactly at the neck opening as a gas collection unit is mounted in its place. The gas collection unit preferably consists of similar materials as a buffer space. One appropriate gas collection unit is disclosed in the Finnish Patent No. 78609.

The flow arriving inside gas collection unit 5 from the buffer space travels towards the respiratory tracts of a patient. As described above, the gas exhaled by a patient is passed through a connecting pipe 13 to a measuring device 10 for measurements. Leaking tends to occur between a patient positioned in neck opening 41 and the skirts extending around the neck opening. When the neck opening is covered by buffer space 11 having an oxygen content equal to that of the gas flowing from port 31 into the gas collection unit, the harmful effect of leaking can be minimized. The essential point is that the oxygen content of incoming gas remains stable. Another advantage gained by a buffer space extending around the entire gas collection unit is the fact that the leaks possibly occurring through fasteners 12 and an opening 22 in hood 38 become insignificant in view of the measurements effected by means of measuring device 10.

Figure 6:
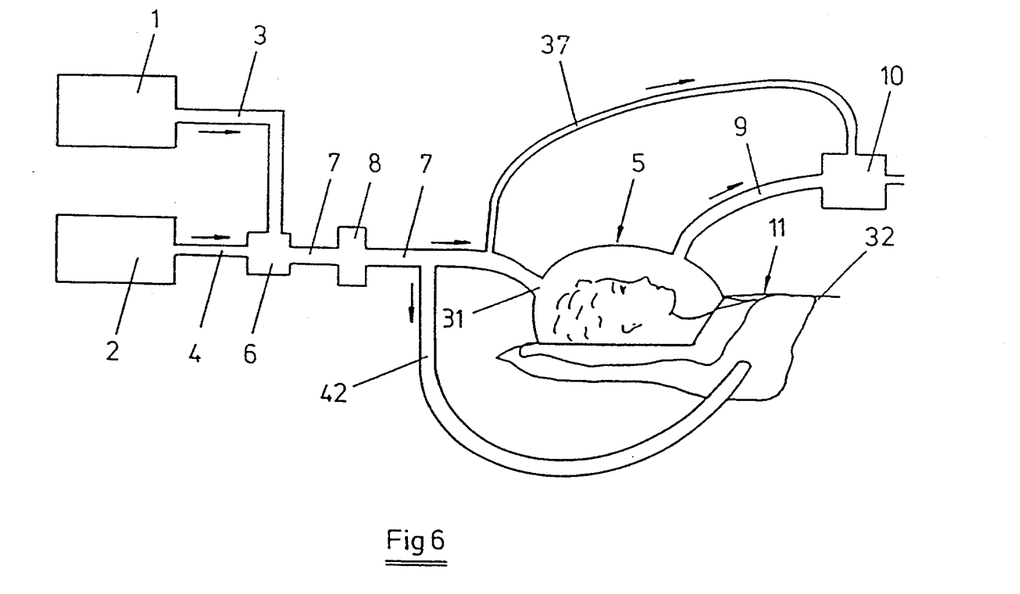
FIG. 6 is a schematic general view of one arrangement alternative to FIG. 1 for metabolic measurements on patients respiring a gas having a higher oxygen content than ambient air.
Figure 7:
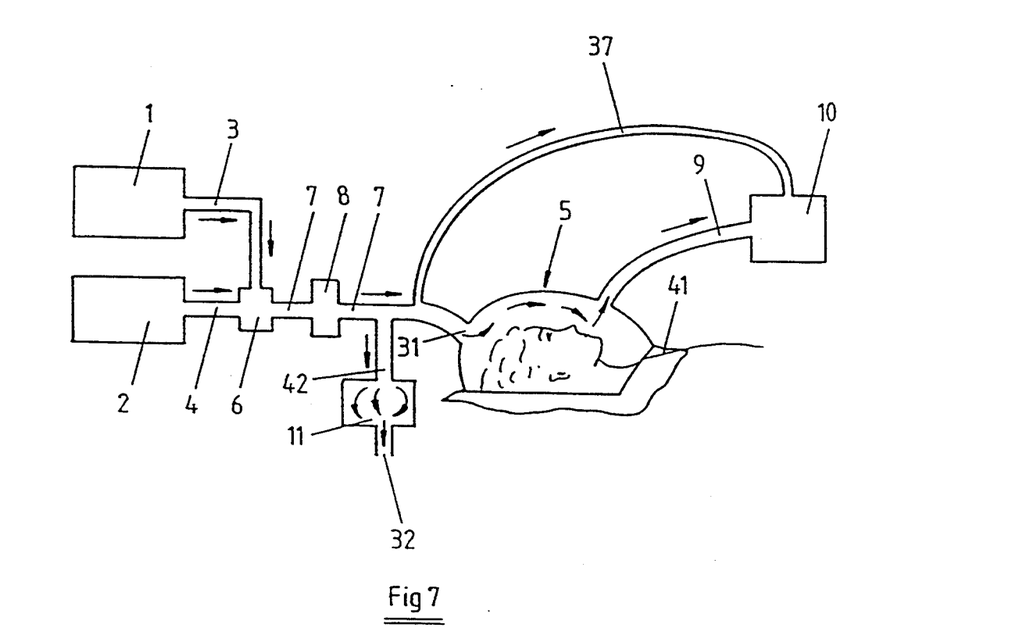
FIG. 7 is a schematic general view of one arrangement alternative to FIGS. 1 and 6 for metabolic measurements on patients respiring a gas having a higher oxygen content than ambient air.

FIGS. 6 and 7 illustrate arrangements alternative to FIG. 1 for delivering an oxygen content higher than ambient air to a patient while maintaining the oxygen content inside gas collection unit 5 as stable as possible. According to FIG. 1, the oxygen is supplied from gas source 1 along line 3 and the air from gas source 2 along line 4 to element 6, wherein the ratio of oxygen and air is adjusted to a desired level. The combined gas flow continues along line 7 to a total gas-flow controlling element 8 and further along line 7 to gas collection unit 5 through a port 31 made in the same. A sample is aspirated from line 7 along a line 37 at a small flow rate to measuring device 10 for analysing the oxygen content of the gas.

The most significant difference in FIG. 6 relative to FIG. 1 is the fact that upstream of gas collection unit 5 some of the gas running along line 7 is deflected along a line 42 to serve as a cover for neck opening 41 of the gas collection unit by building a buffer space 11. Thus, the opening most likely to jeopardize the stability of the oxygen content of a gas collection unit can be covered or screened with a gas having an oxygen content equal to that of a gas arriving in the gas collection unit through port 31. In this case, the gas collection unit itself can be exactly identical to that shown in FIGS. 2 and 3. A buffer space 11 can be designed e.g. by fitting the gas collection unit skirt 34 shown in FIG. 2 with another sheet identical to sheet 40. A gas flow arriving along a line 42 would be brought in between these two sheets.

FIG. 7 illustrates in the same way as FIG. 6 an arrangement, wherein upstream of gas collection unit 5, some of the gas travelling along line 7 is deflected into line 42. Thereafter, unlike in FIG. 7, the gas flowing along line 42 is led away and the by-passing gas is no longer brought to cover the gas collection unit. Thus, the neck opening 41 and other ports of a gas collection unit in communication with ambient air must be sealed completely for preventing leaks. In a preferred case, the by-passing gas flowing along line 42, prior to allowing it to escape, is deflected into buffer space 11 which in the case of FIG. 7 is separated from a gas collection unit. In this case, the object of buffer space 11 is to prevent the access of air through port 32 inside the system all the way into a gas collection unit during a vigorous inhalation. Therefore, in a preferred case the buffer space has a volume which is at least equal to the single respiratory volume of a patient. In the case shown in FIGS. 6 and 7, the buffer space volume must be regarded as including both a line 42 branching off line 7 and extending towards the buffer space and the actual buffer space 11. Thus, a buffer space 11 could consist of a mere line 42 which should only be of sufficient length so that the inner volume of said line would match the single respiratory volume.

Hence, it is essential in terms of the invention that the flow carried through gas collection unit 5 or measuring device 10 is less than the overall flow rate (N l/rain) of gases arriving along lines 3 and 4 or alternatively along one or a plurality of lines 7, before the flow by-passing a gas collection unit branches off this line. Usually, the flow rate running through measuring device 10 is appr. 40 l/min. The amount of gas flowing past a gas collection unit depends on volume (V) of buffer space 11. Theoretically, the overall flow (N) can be equal to that occurring through measuring device 10 if the volume of a buffer space is substantially larger than that of a patient's inhalation or exhalation. Often in practice, however, it must be somewhat larger. In a preferred case, the overall flow (N) should be 25% or 10 l/rain larger than the flow occurring through measuring device 10 or even larger than that.

The invention is by no means limited to the above embodiments but various details of the invention can be modified within the scope of the claims. The invention can be applied not only for supplying a patient with a gas having a different concentration than ambient gas but also for supplying a patient with a gas having a different composition than ambient gas. FIGS. 1, 6 and 7 only illustrate plausible embodiments in supplying a patient with a gas having a higher oxygen content than the environment and in striving to maintain the gas respired by a patient as stable as possible in terms of its oxygen content.

FIGS. 2 and 3 illustrate that gas is delivered from inside a gas collection unit to measuring device 10 directly through ports 22 and 21 made in hood 38 and buffer space hood 33. The location of these ports 22 and 21 in hoods 38 and 33 can be re-positioned as required. It is also obvious that a line 9 leading to the measuring device can be extended directly into a gas collection unit through the same openings 32 and 41 which are used to fit a gas collection unit and a buffer space around the head of a patient whereby the measuring device receives the gas, not by an inlet pierced through the gas collection unit, but instead by way of a port 22 provided in line 9. Unlike in FIGS. 6 and 7, the gas flowing into a gas collection unit along line 7 can be directed, not by way of opening 31 penetrating through a gas collection unit, but in a manner that said line 7 is extended through opening 41, whereby said opening or port 31 is located in line 7. In the case of FIGS. 1, 2 and 3, wherein said buffer space 11 is located around a gas collection unit, said line 7 carrying gas into the buffer space can be extended through neck opening 41 into a gas collection unit as long as the gas is first allowed to flow freely and to mix inside the buffer space. Even in that case, a gas collection unit need not be provided with any extra openings or ports but a port 31 shown in the figures is located in such a line 7 which carries the gas into a gas collection unit. The same way, a port 21 penetrating through the buffer space for flowing the gas therein can be replaced with a line 9 entering through opening 32.

FIGS. 2 and 3 illustrate one preferred embodiment for a gas collection unit and a buffer space. There are several possible designs, one of which has already been described in reference to FIG. 6. In FIGS. 1, 2 and 3, said buffer space 11 is provided with just a single line 7 to receive a gas to be delivered to a patient but it is obvious that the oxygen gas and air can be carried by separate lines 7 extending from gas sources 1 and 2 into a buffer space, where such gases have sufficient time to mix prior to advancing into a gas collection unit. When employing separate lines 7 leading to a buffer space, there is no need for lines 3 and 4, extending from gas sources 1 and 2 and merging into a single line 7, as shown in FIG. 1. In this case, it should also be preferable to pick up samples from the inlet opening 31 of gas collection unit 5 for measuring the oxygen content.

We claim:

1. A method for supplying a mixture of gases from sources of the gases along a gas flow path to the interior of a gas collection unit for respiration by a patient, the gas collection unit having at least one location at which the ingress of ambient air into the interior of the gas collection unit may occur, said method comprising the steps of:

providing gases from the sources of the gases to the gas flow path;

mixing the gases to form a mixture of gases in the gas flow path;

flowing a first portion of the mixture of gases along the gas flow path into the interior of the gas collection unit for respiration by the patient;

establishing a gas buffer volume in fluid communication with the gas flow path at a point in the gas flow path upstream of the gas collection unit;

discharging a second portion of the mixture of gases from the gas buffer volume to bypass the second portion of the mixture of gases away from the interior of the gas collection unit;

supplying the second portion of the gas mixture to the gas collection unit location so that gas flow of the second portion of the mixture of gases at the location will act to reduce the ingress of ambient air into the interior of the gas collection unit at the location; and providing the gases exhaled by the patient in the interior of the gas collection unit to a measuring unit.

2. A method as set forth in claim 1 wherein the step of establishing the gas buffer volume is further defined as establishing the gas buffer volume along the gas flow path in series with the gas collection unit so that said first and second portions of the mixture of gases pass through the gas buffer volume.

3. A method as set forth in claim 1 wherein the step of establishing the gas buffer volume is further defined as establishing the fluid communication of the gas buffer volume to the gas flow path as a branch of the gas flow path so that only the second portion of the mixture of gases flows through the gas buffer volume.

4. A method according to claim 1 wherein the step of mixing the gases is further defined as mixing the gases upstream of the point of fluid communication of the gas buffer volume with the gas flow path.

5. A method as set forth in claim 1 wherein the gas collection unit has an exterior and wherein the step of establishing a gas buffer volume is further defined as establishing a gas buffer volume on the exterior of the gas collection unit.

6. A method as set forth in claim 1 wherein the gas collection unit has an opening formed to receive the neck of the patient and wherein the step of supplying the second portion of the gas mixture to the gas collection unit location is further defined as supplying the second portion to a location adjacent the opening for the neck of the patient.

7. The method according to claim 1 wherein the step of providing gases is further defined as providing gases comprising oxygen and a nitrogen containing gas.

8. A method as set forth in claim 7 wherein the step of providing the gases is further defined as providing oxygen and a nitrogen containing gas comprising air.

9. A method as set forth in claim 7 further defined as mixing the gases to form a mixture of gases containing more oxygen than is present in ambient air.

10. A method as set forth in claim 7 further including the step of measuring the oxygen content of the mixture of gases.

11. A method as set forth in claim 10 further including the step of measuring the oxygen content and carbon dioxide content of the gases exhaled by the patient.

12. A method as set forth in claim 11 wherein the measuring step is further defined as determining the respiratory quotient of the patient.

13. A method as set forth in claim 1 wherein the inhalation and exhalation occurring during the respiration of the patient in the interior of the gas collection unit can alter the amount of the first portion of the gas mixture flowing into the gas collection unit and wherein the step of establishing the gas buffer volume is further defined as establishing a gas buffer volume of sufficient volumetric magnitude so that the amount of gases flowing in the gas flow path upstream of the point of fluid communication of the gas buffer volume is sufficient to buffer the first portion of the mixture of gases against alterations resulting from the respiration of the patient.

14. A method as set forth in claim 13 wherein the step of providing gases from the gas sources is further defined as providing a quantity of gases to the gas flow path upstream of the point of fluid communication of the buffer volume that is at least 25% greater than the first portion of the mixture of gases.

15. A method as set forth in claim 13 wherein the step of establishing the gas buffer volume is further defined as establishing a gas buffer volume having a volumetric magnitude at least equal in size to the respiratory volume of the patient.

16. A method as set forth in claim 15 wherein the step of establishing a gas buffer volume is further defined as establishing a gas buffer volume of at least 3 liters.

17. A method for supplying a mixture of gases from sources of the gases along a gas flow path to the interior of a gas collection unit for respiration by a patient, the inhalation and exhalation occurring during the respiration of the patient being capable of altering the amount of gas flowing into the gas collection unit, said method comprising the steps of:

flowing gases from the sources of the gases to the gas flow path;

mixing the gases to form a mixture of gases in the gas flow path;

providing a first portion of the mixture of gases along the gas flow path to the interior of the gas collection unit for respiration by the patient;

establishing a gas buffer volume in fluid communication with the gas flow path at a point in the gas flow path upstream of the gas collection unit, said gas buffer volume having a volumetric magnitude such that the amount of gases flowing in the gas flow path upstream of the point of fluid communication of the gas buffer volume is sufficient to buffer the first portion of the mixture of gases against alterations resulting from the respiration of the patient;

discharging a second portion of the mixture of gases from the gas buffer volume to bypass the second portion of the mixture of gases from the interior of the gas collection unit; and providing the gases exhaled by the patient in the interior of the gas collection unit to a measuring unit.

18. A method as set forth in claim 17 wherein the step of providing gases from the gas sources is further defined as providing a quantity of gases to the flow path upstream of the point of fluid communication of the buffer volume that is at least 25% greater than the first portion of the gases.

19. A method as set forth in claim 17 wherein the step of establishing the gas buffer volume is further defined as establishing the gas buffer volume along the gas flow path in series with the gas collection unit so that the first and second portions of the mixture of gases pass through the gas buffer volume.

20. A method as set forth in claim 17 wherein the step of establishing the gas buffer volume is further defined as establishing the fluid communication of the gas buffer volume to the gas flow path as a branch of the gas flow path so that only the second portion of the mixture of gases flows through the gas buffer volume.

21. A method as set forth in claim 17 wherein the gas collection unit has an exterior and wherein the step of establishing a gas buffer volume is further defined as establishing a gas buffer volume on the exterior of the gas collection unit.

22. A method as set forth in claim 17 wherein the step of establishing the gas buffer volume is further defined as establishing a gas buffer volume having a volumetric magnitude at least equal in size to the respiratory volume of the patient.

23. A method as set forth in claim 22 wherein the step of establishing a gas buffer volume is further defined as establishing a gas buffer volume of at least 3 liters.

24. Apparatus for supplying a mixture of gases from a source of the gases for respiration by a patient, the apparatus providing the gases exhaled by the patient to a measuring unit, said apparatus comprising:

means forming a gas flow path for said apparatus, said gas flow path means being couplable to the sources of the gases;

a gas collection unit having an interior for receiving the head of the patient, said gas collection unit having an inlet port for receiving a first portion of the gases provided by the gas flow path means for respiration by the patient, said gas collection unit having an outlet port for discharging the gases exhaled by the patient to the measuring unit, said gas collection unit having at least one location at which the ingress of ambient air into the interior of said gas collection unit may occur;

gas buffer volume means coupled in fluid communication with said gas flow path means at a point upstream of the gas collection unit, a second portion of the gases being discharged from said gas buffer volume means to bypass the second portion of the gases away from the interior of the gas collection unit; and discharge means supplying the second portion of the gases to the gas collection unit location so that gas flow of the second portion of the mixture of gases at the location will act to reduce the ingress of ambient air into the interior of the gas collection unit at the location.

25. An apparatus as set forth in claim 24 wherein said gas collection unit has an opening formed to accommodate the neck of the patient and wherein said discharge means supplies the second portion of the gases to a gas collection unit location adjacent said opening for the neck of the patient.

26. An apparatus as set forth in claim 24 wherein said gas buffer volume means is coupled to said gas flow path means in series with said gas collection unit to contain said first and second portions of the gases, said inlet port of said gas collection unit receiving said first portion of said gases from said gas buffer volume means.

27. An apparatus as set forth in claim 24 wherein said gas flow path means has a branch in which said gas buffer volume means is located for receiving and discharging only the second portion of the gases.

28. An apparatus as set forth in claim 24 wherein said gas collection unit has an exterior and wherein said gas buffer volume means is mounted on the exterior of the gas collection unit.

29. An apparatus as set forth in claim 28 wherein said gas collection unit has a portion formed to fit over the face of the patient and wherein said gas volume buffer means is mounted on at least part of said portion of said gas collection unit.

30. Apparatus for supplying a mixture of gases from sources of the gases for respiration by a patient, the apparatus providing the gases exhaled by the patient to a measuring unit, the inhalations and exhalations occurring during the respiration of the patient being capable of altering the amount of gases flowing to the patient, said apparatus comprising:

means forming a gas flow path for said apparatus, said gas flow path means being couplable to the sources of the gases;

a gas collection unit having an interior for receiving the head of the patient, said gas collection unit having an inlet port for receiving a first portion of the gases provided by the gas flow path means for respiration by the patient, said gas collection unit having an outlet port for discharging gases exhaled by the patient to the measuring unit; and gas buffer volume means coupled in fluid communication with said gas flow path means at a point upstream of the gas collection unit, said gas buffer volume means discharging a second portion of the mixture of gases from the gas buffer volume means to bypass the second portion of the gases away from the interior of the gas collection unit, said gas buffer volume means having a volumetric magnitude sufficient to buffer the first portion of the gases against alterations in amount resulting from the respiration of the patient.

31. An apparatus as set forth in claim 30 wherein said gas buffer volume means is coupled to said gas flow path means in series with said gas collection unit to contain said first and second portions of the gases, said inlet port of said gas collection unit receiving said first portion of said gases from said gas buffer volume means.

32. An apparatus as set forth in claim 30 wherein said gas flow path means has a branch in which said gas buffer volume means is located for receiving and discharging only the second portion of the gases.

33. An apparatus as set forth in claim 30 wherein said gas buffer volume means is further defined as having a volumetric magnitude at least equal to the respiratory volume of the patient.

34. An apparatus as set forth in claim 33 wherein said gas buffer volume means is further defined as having a volumetric magnitude of at least 3 liters.

35. An apparatus as set forth in claim 30 wherein said collection unit has an exterior and wherein said gas buffer volume means is located on the exterior of said gas collection unit.

36. An apparatus as set forth in claim 35 wherein said gas collection unit has a portion formed to be placed over the face of the patient and wherein said gas buffer volume means covers at least part of said portion of said gas collection unit.

* * * * *